United States Patent
Reiter et al.

(10) Patent No.: US 6,510,727 B2
(45) Date of Patent: Jan. 28, 2003

(54) ARRANGEMENT FOR THE QUANTITATIVE AND QUALITATIVE ANALYSIS OF PARTICLES IN GASES

(75) Inventors: Christian Reiter, Graz (AT); Herbert Thanner, Graz (AT)

(73) Assignee: AVL List GmbH, Graz (AT)

( * ) Notice: Subject to any disclaimer, the term of this patent is extended or adjusted under 35 U.S.C. 154(b) by 75 days.

(21) Appl. No.: 09/736,626

(22) Filed: Dec. 14, 2000

(65) Prior Publication Data

US 2002/0124632 A1 Sep. 12, 2002

(30) Foreign Application Priority Data

Dec. 14, 1999 (AT) ................................................ 2101/99

(51) Int. Cl.[7] .................. G01N 33/00; G01N 27/00; G01N 37/00
(52) U.S. Cl. .................. 73/24.03; 73/24.06; 73/28.01; 73/28.05; 73/863.22
(58) Field of Search .................. 73/23.31, 23.33, 73/24.01, 24.03, 24.06, 28.01, 28.02, 28.05, 28.06, 863.22, 865.5, 865.8, 864.71

(56) References Cited

U.S. PATENT DOCUMENTS

| | | | | |
|---|---|---|---|---|
| 3,561,253 A | * | 2/1971 | Dorman | 73/28.05 |
| 3,590,629 A | * | 7/1971 | Courbon | 73/28.05 |
| 3,653,253 A | * | 4/1972 | Olin | 73/24.03 |
| 3,715,911 A | * | 2/1973 | Chuan | 73/28.05 |
| 3,805,591 A | * | 4/1974 | Willis et al. | 73/24.03 |
| 3,854,321 A | * | 12/1974 | Dahneke | 73/28.01 |
| 4,446,720 A | * | 5/1984 | Sinclair | 73/24.06 |
| 5,056,355 A | * | 10/1991 | Hepher et al. | 73/28.05 |
| 5,892,141 A | * | 4/1999 | Jones et al. | 73/24.03 |

FOREIGN PATENT DOCUMENTS

SU 1594381 * 9/1990 ................ 73/24.03

* cited by examiner

Primary Examiner—Daniel S. Larkin
(74) Attorney, Agent, or Firm—Sonnenschein Nath & Rosenthal

(57) ABSTRACT

An arrangement is described for the quantitative and qualitative analysis of particles in gases, especially of particles in the exhaust gas of internal combustion engines, comprising a vibrating system with at least one vibration sensor, preferably a piezoelectric resonator, which is provided with at least one collecting surface for the particles to be analyzed, a circuit for the determination of characteristic vibration parameters as well as guide and transport arrangements for the gas to be analyzed. In order to obtain as large as possible a measuring range with a linear characteristic line and therewith a great sensitivity and dynamics with respect to the mass load in the entire measuring range, there is provided a vibration sensor stationary relative to the measuring chamber, and at least one active deflecting device for the gas or the particles contained in the gas.

28 Claims, 6 Drawing Sheets

ARRANGEMENT FOR THE QUANTITATIVE AND QUALITATIVE ANALYSIS OF PARTICLES IN GASES

BACKGROUND OF THE INVENTION

The invention relates to an arrangement for the quantitative and qualitative analysis of particles in gases, especially of particles in the exhaust gas of internal combustion engines, comprising a vibrating system with at least one vibration sensor, preferably a piezoelectric resonator, which is provided with at least one active collecting surface for the particles to be analyzed, which, through at least one outlet opening, enter the measuring chamber containing the vibration sensor, a circuit for determining characteristic vibration parameters, as well as guide and transport arrangements for the gas to be analyzed; as well as a process for the quantitative and qualitative analysis of particles in gases, especially of particles in the exhaust gas of internal combustion engines, in which the particles are precipitated through at least one outlet opening onto at least one active collecting surface of at least one stationary vibration sensor, preferably a piezoelectric resonator, of a vibration system, and by the particle precipitation there is determined the change of characteristic vibration parameters.

The measuring of particle emissions which arise in the combustion process of organic material has been of great interest for many years. The influence on human health of particles that are present in the breathing air stands at present at the center of many scientific investigations. Since the particles can be conceived as the measure of an incomplete combustion process, it is possible to raise the efficiency only by a continuous optimization of the combustion process and therewith to reduce the particle emission. From this continuous optimization there results high demands on the particle measuring system with regard to resolution, measuring range and dynamics. With vibration sensors, such as piezoelectric resonators for example, it is possible to determine the foreign mass applied directly to the sensor surface by means of the thereby occurring frequency change. In order to be able to measure the particle mass and/or the concentration of particles, with the aid of a probe, a certain volume of air is drawn through a particle collector. This measurement can be executed in one stage, so that if possible all the particles in the air stream are precipitated on a resonator, or in several stages, in which case here advantageously particles in defined size classes are precipitated on several resonators, wherewith not only the mass is determinable, but also a classification according to particle size is possible. The precipitation can occur, for example, by electrostatic processes, i.e., acceleration of the particles in the electric field onto the oscillating crystal, as is described, in U.S. Pat. No. 5,892,141.

The precipitation characteristic on the resonator collecting surface is given, in the case of gas samples fed-in through an opening, such as a nozzle or the like, directly over the resonator surface (an example for this is given in document U.S. Pat. No. 3,561,253), in addition to the flow-through, by the particle size, the geometry of the opening and its distance from the surface of the resonator. Even with several openings per resonator surface, as is disclosed in U.S. Pat. No. 4,446,720, after an initially linear decrease of the frequency, with rising particle load of the resonator, the frequency change above about 100 Hz begins to follow an exponential course.

In the article "Applications of Piezoelectric Quartz Crystal Microbalances" in "Methods and Phenomena, Their Applications in Science and Technology", vol. 7, Elsevier 1984, an arrangement is described in which the vibration crystal is moved horizontally under a precipitation nozzle by means of a motor, in order to achieve a more uniform distribution of the particles. In such an arrangement, a relatively long period of time of several seconds is required until several layers of particles are precipitated, or the vibrating crystal must be moved back and forth very rapidly, for which purpose the arrangement must be built very stable and massive, and therewith correspondingly complicated and ill-suited for mobile use.

Also, from further documents on the state of the art, such as U.S. Pat. No. 5,056,355, no guiding arrangement for the gas stream is to be derived with which a control of the gas stream and therewith also of the particle stream would be possible to implement.

Likewise with the gas detector of DE 31 06 385, no arrangement is present which makes possible such a control of the impact zone of the particles over the collecting surface of the vibration sensor. On the contrary, it is a matter in this reference of a passive deflecting arrangement which does, to be sure, deflect the gas stream so that the latter will definitely pass onto the vibration sensor, but which then, however, permits no further influencing or control of the gas stream.

SUMMARY OF THE INVENTION

The problem of the present invention, therefore, is an arrangement and a process for the analysis of particles in gases, which with avoidance of the disadvantages of the state of the art, offers with a very simple and easy construction, as great as possible a measuring zone with a linear characteristic curve and therewith a great sensitivity and dynamics with respect to the mass loading in the entire measuring zone.

For the solution of this problem, the inventive arrangement described at the outset is characterized in that there are provided vibration sensors stationary with respect to the measuring chamber, and at least one active guiding and steering device for the gas or the particles contained therein. Therewith, despite a simple and easy construction, there can be achieved a uniform distribution of the precipitated particles over the active collecting surface of the vibration sensor, and therewith the desired wide measuring range with a linear characteristic curve and a high sensitivity and dynamics. Through the movement of the impact zone of the particles over the active collecting surface of the vibration sensor, the linear range of the frequency change by particle load can be significantly extended, since the saturation of individual zones can be avoided or at least be drawn out much longer than with conventional systems.

A first, structurally very simple and dependable form of execution of the arrangement according to the invention is characterized in that as an active guiding and controlling device there is provided a shutter with at least one shutter opening, the transversable cross section area of which is small as compared to the active collecting surface of the vibration sensor, in combination with an arrangement that moves the shutter relative to the active collecting surface of the vibration sensor, in which arrangement the movement runs essentially parallel to the active collecting surface of the vibration sensor.

According to a further feature of the invention, an arrangement is provided for the movement of the shutter, which moves at least one shutter opening on a closed path. Therewith, with as little as possible structure height, there can be achieved a uniform precipitation over a large surface area of the active vibration sensor surface.

In order to obtain s simple built arrangement, which is also attuned to the typically circular active collecting surfaces of the vibration sensors, there is provided an arrangement for the movement of the shutter, which moves at least one of the shutter openings over an essentially circular path, in which the axis of the circular movement is normally oriented essentially perpendicular to the active collecting surface.

Altogether it is provided there that the vibration sensor, and/or its active collecting surface, is advantageously constructed rotationally symmetrical about the axis of the circular movement, whereby there is achieved an optimal utilization of the collecting surface.

If, according to a further feature of the invention, an arrangement for moving the shutter is provided, which moves at least one shutter opening along a path that arises through the superposing of at least two rotary movements with essentially parallel axes of rotation, which axes of rotation are oriented essentially perpendicular to the active collecting surface, there can be achieved a still better and also more uniform surface coverage for the precipitation onto the active collecting surface of the vibration sensor, and that in a relatively short time.

According to a further feature of the invention, it is provided that an arrangement for the movement of the shutter relative to the vibration sensor is provided with an alternating speed, or with an alternating angular velocity.

For devices with electrostatic precipitation, the corona needle, present in any case, can be coupled according to the invention with arrangements for its movement relative to the vibration sensor, so that by reason of these movements, the electric field is continuously varied, and in this manner brings about the desired alteration of the impact zone of the particles on the vibration sensor. In this form of execution, additional components for the deflection of the gas jet or of the particles are avoided insofar as possible, whereby a light arrangement results, with which also the susceptibility to malfunctioning and the maintenance expenditure are again reduced.

According to a further form of execution of the invention, the arrangement can also be characterized in that as an active guiding and steering device, there is provided at least one arrangement for the generation of a variable electrical magnetic or electromagnetic field between the outlet opening and the vibration sensor, as well as an arrangement for the electrical charging of the particles in the gas. In order to obtain a defined deflection or altogether a deflection of the particles also for normally neutral particles, the particles should be electrically charged before reaching the outlet opening. This charge can occur mono-polarly or bi-polarly by a corona discharge or a radioactive source. With this form of execution, movable parts can be avoided to the greatest possible extent and therewith the weight of the apparatus, the susceptibility to malfunctioning, and the expenditure for its maintenance, can be significantly reduced. Further, in a simple manner and without complicated mechanical intervention, the path of the particle beam can be altered or adapted.

According to a further form of execution of the invention there is provided as an active guide and steering device, at least one outlet opening for an additional gas jet, preferably to the side of the opening for the entry of the particles, in which case the axes of the outlet openings preferably enclose between them an angle not equal to zero, or there can also be provided an active guide and steering device for the generation of an alternating current speed and/or direction. A further form of execution is presented by an arrangement in which the devices for the generation of alternating gas or of particle speeds are provided in the entry opening.

The process for particle analysis in gases described at the outset is characterized, according to the invention, in that during the measuring period, the particle jet is moved actively over an ever-alternating zone of the collecting surface of the vibration sensor. Thereby, a local saturation of the active collecting surface of the vibration sensor is avoided, the particles are distributed more uniformly on the active collecting surface and from this there results a substantial widening of the linear constituent of the measuring range, with higher sensitivity and dynamics with respect to the mass load over the entire measuring range.

Advantageously there, according to a further feature of the invention, it is provided that the particle jet is led along a closed curve, whereby a very uniform precipitation over a large surface area of the active collecting surface of the vibration sensor can be achieved with as small as possible a construction height if, according to a further feature of the invention, over the time interval of the measurement, an ever-alternating zone of the active collecting surface of the vibration sensor is excepted from the shielding, which zone defines a closed curve.

An especially simple variant there, which also takes into consideration the typical form of the active collecting surfaces of the vibration sensors, is characterized in that the particle jet is led along a circular path.

According to another development of the inventive process, the particle jet is led along a curve which arises by the superposing of at least two rotary movements with axes of rotation perpendicular to the active collecting surfaces. With this development there can be achieved a still better and also more uniform surface coverage for the precipitation of the particles on the active collecting surface of the vibration sensor, and that in a relatively short time.

Advantageously it is provided in all these variants that the particle jet is guided with an alternating speed, or with an alternating annular velocity.

In a variant embodiment of the invention with electrostatic precipitation, the electric field used for ionization of the particles can be continuously altered, so that therewith there occurs a change of the impact zone of the particle jet on the active collecting surface of the vibration sensor.

According to a further form of execution of the inventive process, there is provided, additionally to or alternatively to the above-described features, that the particle jet is deflected by an alternating electrical, magnetic, or electromagnetic field and led over the active collecting surface of the vibration sensor.

According to a further feature of the invention, it can also be provided that a gas jet of alternating flow speed and/or direction is directed onto the particle jet, and that the latter is therewith deflected.

BRIEF DESCRIPTION OF THE DRAWINGS

In the following description some preferred examples of execution are to be explained in detail with reference to the drawing.

FIG. 1 shows a schematic representation of a device according to the invention in side view.

FIG. 2 is a schematic representation in plan view of a shutter for an arrangement according to the invention.

FIG. 3*a* shows the precipitation pattern of the shutter of FIG. 2 in a stationary application.

FIG. 3b shows the precipitation pattern with rotation of the shutter of FIG. 2 about its central axis.

DETAILED DESCRIPTION OF THE PREFERRED EMBODIMENTS

Figure 1:
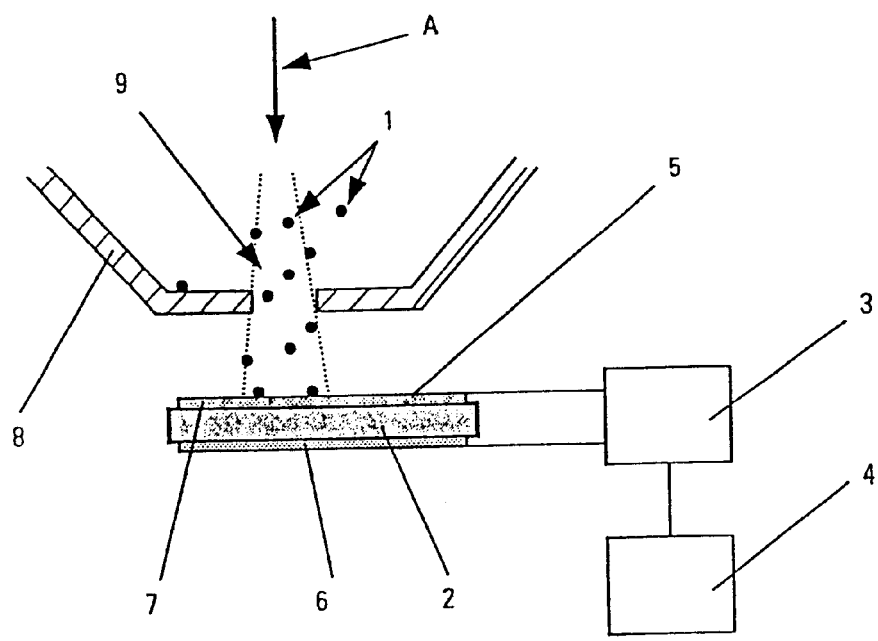

Over conventional sample-taking devices containing usual-type conducting and transport arrangements 18, suction pumps, and the like for the gas A laden with the particles 1 to be analyzed, this gas is brought into a chamber 20 in which a vibrating system is present, in which, by the mass loading of a sensitive collecting surface of a vibration sensor 2, there comes about a change of the acoustic parameters of the vibration sensor 2. Pulsed or also continuous vibration excitation can be used. The parameters of the collecting surfaces comprise, for example, the thickness, the surface mass density, the mechanical impedance on the surface, or the speed of sound in the zone of the surface, whereby according to the type of vibrating system, i.e., volume or surface vibrating systems, there result changes of the resonance frequency or of the appertaining period duration, of the running time of the sound pulse or the like. These changes are detected on the electro-acoustic converter of the vibrating system and then drawn upon in a manner known per se for the determination of the mass loading. One of the typically used vibrating systems contains a piezoelectric resonator with a piezoelectric vibration sensor 2. The piezoelectric resonator is further provided, inter alia, with an oscillator circuit 3 and a switching arrangement 4, for the control of the oscillator circuit 3 as well as for the recording, storing, and displaying of the measurement data.

On the piezoelectric vibration sensor 2 there is mounted a collecting electrode 5 as an active collecting surface for the particles 1 to be analyzed and, on the side of the resonator 2 lying opposite the collecting electrode 5 there is mounted a counter-electrode 6. The collecting electrode 5 is constructed preferably as an open-pored structure with pores. In the pores, there are captured the particles that are collected by electrostatic precipitation or by impaction on the piezoelectric resonator 2, wherein advantageously the size of the pores of the collecting electrode 5 is adapted to the size to be expected of the particles to be measured.

Obviously the collecting electrode 5, and this holds also for the counter-electrode 6, does not have to be provided directly on the active section of the piezoelectric vibration sensor 2, but could also be mounted on a non-piezoelectrically active extension, preferably with an optimal effect on the change of the resonance frequency on the side lying opposite the clamp of the sensor to the oscillator circuit 3.

The described piezoelectric resonator can be constructed on the basis of Volume (BAW—Bulk Acoustic Waves) or surface vibration systems (SAW—Surface Acoustic Waves), in which case, through the mass loading of the piezoelectric vibration sensor with the particles to be analyzed, there occurs a change of the resonance frequency or of the appertaining period duration. For other vibrating systems, in which the running time of a sound pulse altered in each case according to mass loading is measured, surface vibrating systems (SAW) are of primary importance.

At a short distance above the active collecting surface 5 of the vibration sensor 2, there is arranged at least one shutter 8 as a deflecting device, the shutter includes at least one shutter opening 9 which has an outlet opening for the particles 1, a cross sectional area that is less than the area of the active collecting surface 5. Preferably, the cross section of the shutter opening or openings 9 is very small with respect to the active collecting surface 5. In each case, by reason of the shutter opening 9, the impact zone of the particles 1 which move in the direction of the arrow A toward the vibration sensor 2, is narrowly limited on the active collecting surface 5. The shutter or shutters 8 or their outlet opening 9 is movable relative to the stationary vibration sensor 2 and therewith in the course of the precipitation of the particles 1, is moved over the active collecting surface 5 of the vibration sensor 2, essentially parallel to the surface 5, so that the impact zone not shielded by the shutter opening 9 is correspondingly shifted over the active collecting surface 5, and therewith the particle jet is led over the active collecting surface 5 or the vibration sensor 2.

Figure 2:
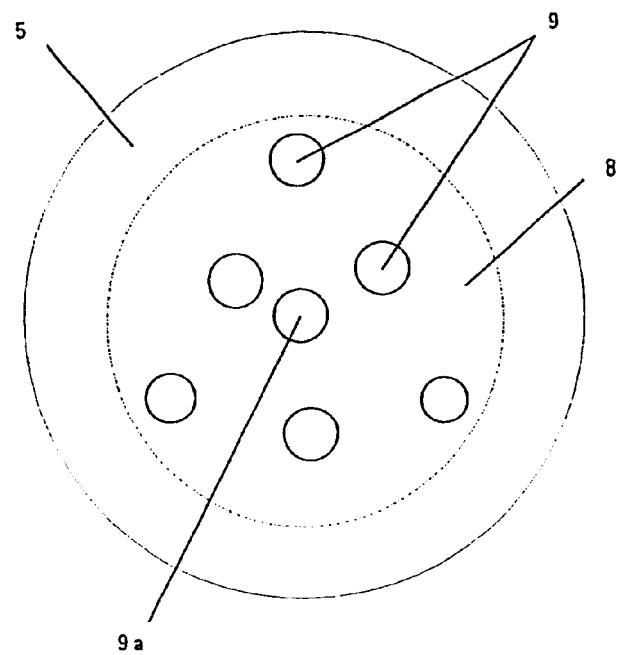
Figure 3A:
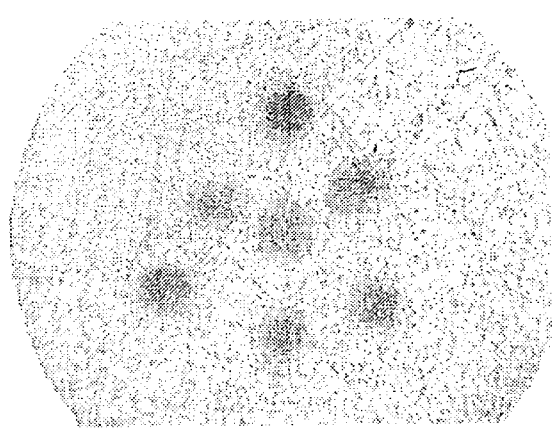
Figure 3B:
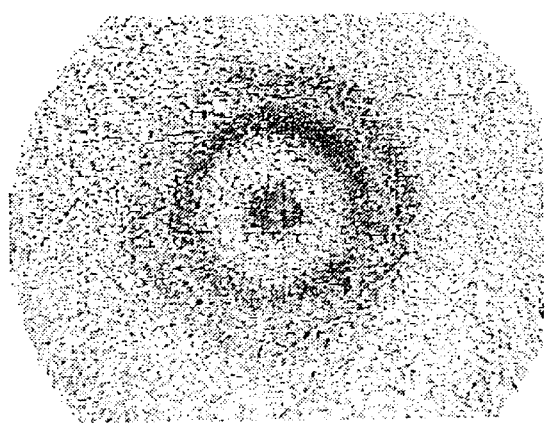

It is advantageous, as is to be seen in FIG. 2, to provide above the active collecting surface 5 of the vibration sensor 2 (not represented in FIG. 2) a shutter 8 with several shutter openings 9, which shutter 8 in this case about its central axis, in the zone of the central shutter opening 9a, rotates and this manner, in the course of the particle precipitation, it directs the particle jets emerging from these shutter openings 9 over different zones of the active collecting surface 5. The central axis of rotation of the shutter 8 is oriented essentially perpendicular to the active collecting surface 5 of the vibration sensor 2. FIGS. 3a and 3b show the precipitation pattern achievable with the shutter of FIG. 2 on the active collecting surface 5, wherein FIG. 3a shows the precipitation pattern with a fixed shutter, as the pattern can also be achieved at best in conventional devices with several nozzles for the gas in-feeding. By reason of the larger-surface precipitation by means of the shutter movable according to the invention, as shown for example, in FIG. 3b, by reason of the clear retardation of saturation effects, there can be achieved an increase of the linear zone of the frequency change of the vibration sensor and a greater sensitivity and dynamics over this increased zone.

Figure 4:
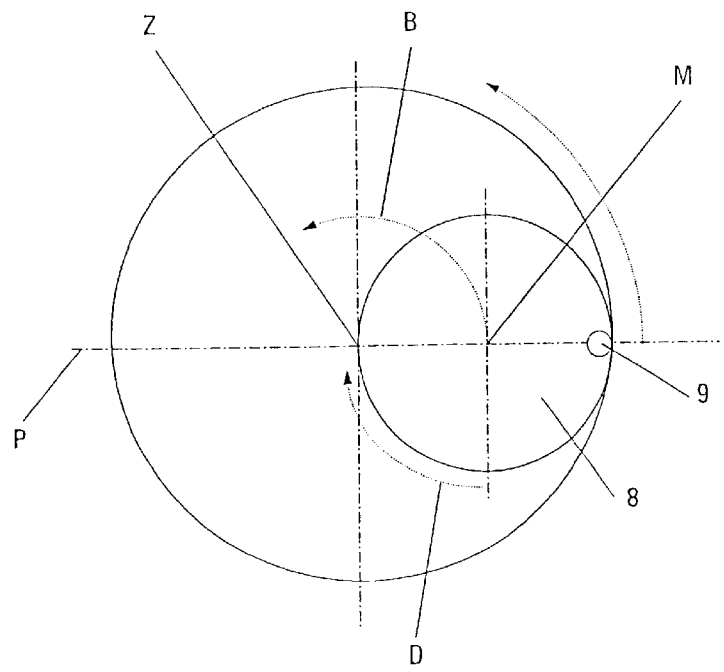
FIG. 4 shows a schematic representation of a shutter arrangement with superposition of two rotary movements.

Obviously, not only circular movements or in general movements of the shutter 8 along closed paths are conceivable. Thus, for example, movements of at least one shutter opening 9 are also possible, which movements arise through the superposing of at least two movements, preferably rotary movements. An example for such a superposition of two rotary movements is explained in connection with FIG. 4. The shutter 8 here with, by way of example, only a single shutter opening 9 rotates above the active collecting surface 5 about the central axis of rotation Z oriented perpendicular to the active collecting surface 5. There, the center M of the shutter 8 moves along the circular path B. Since now the shutter 8 itself rotates again about an axis substantially parallel to the axis Z and passing through its center M in reversed turning direction, symbolized by the arrow D, there is yielded, with corresponding attuning of the angular velocities, a pendulum movement along the line P of the shutter opening 9 over the active collecting surface 5 of the vibration sensor 2. For other relations of angular velocities or like turning direction of both movements there is yielded, however, a rosetta-type movement of the shutter opening 9 relative to the vibration sensor 2, whereby the particles are precipitated with more surface coverage.

Figure 5:
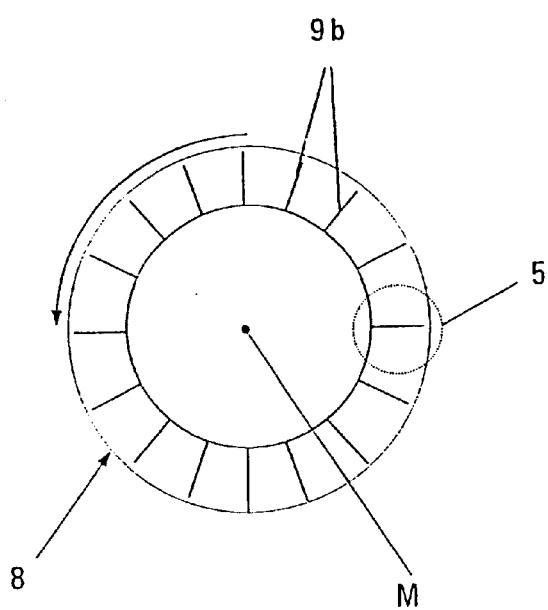
FIG. 5 shows a plan view of an alternate embodiment of a shutter according to the invention.

Another form of execution of a shutter 8 for an arrangement according to the invention is represented in FIG. 5. Here the shutter size is considerably greater than the active collecting surface 5 of the vibration sensor 2, in which of course also several vibration sensors 2 and/or active collecting surface zones 5 could be provided in the here circular movement zone of the shutter openings 9b. The individual shutter openings 9b are present in the form of lengthwise slots proceeding radially from the center of the shutter 8, through which there also runs the axis of rotation oriented essentially perpendicular to the active collecting surface 5 or to each active collecting surface 5. By corresponding guide arrangements it is brought about that always only that zone of the shutter 8 is traversed by the particle jet which lies above an active collecting space zone 5. By reason of the slot-form shutter openings 9b and of their guidance in circular arcs over the active collecting surface 5 by reason of the described geometry, the particles 1 are precipitated on the active collecting surface 5 in strips with a width which corresponds to the length of the slot-form shutter openings 9b, and in a number of layers which corresponds to the number of slot run-throughs during the measurement duration.

Figure 6:
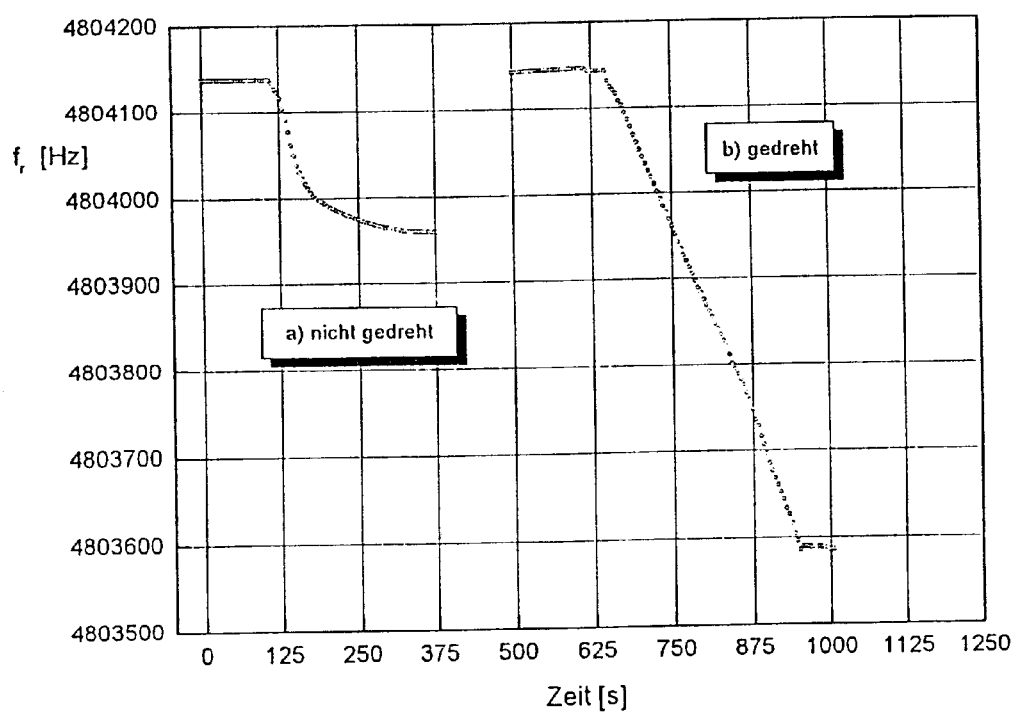
FIG. 6 is a time-frequency diagram with comparison of conventional arrangements with the arrangement according to the invention.

The time-frequency diagram of FIG. 6 explains the advantages and effects of the arrangement according to the invention. There the left curve corresponds to a measurement with a stationary shutter 8 as it is represented in FIG. 2, and the precipitation pattern of which corresponds to that of FIG. 3a. After a brief measuring time, the frequency caused by the increasing mass loading of the active collecting surface of the vibration sensors changes from a linear course to an exponential course with still only the slightest frequency change on further mass loading. In contrast to this, the right curve of FIG. 6, which has been determined by a measurement with a shutter 8 of FIG. 2, rotated about its axis, shows that through the rotation and therewith the distribution of the precipitated particles in correspondence to a pattern as in FIG. 3b, a substantial lengthening of the linear zone is achievable, here a quintuple lengthening, from about 100 Hz to about 500 Hz.

Obviously, the deflection of the particle jet from the outlet opening 9 does not necessarily have to be effected by a movement of this outlet opening. Thus, it is also conceived that the particles are deflected by the forces acting on them directly during their movement, and the particle jet is constructed in this manner. Thus, for example, as a deflecting device there can be provided arrangements for the generation of a variable electric, or magnetic, or electromagnetic field between the outlet opening 9 and the vibration sensor 2.

Figure 7:
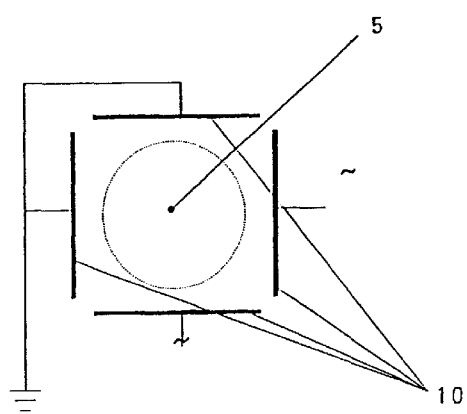
FIG. 7 shows a schematic view of an embodiment with electrical deflection.
Figure 8:
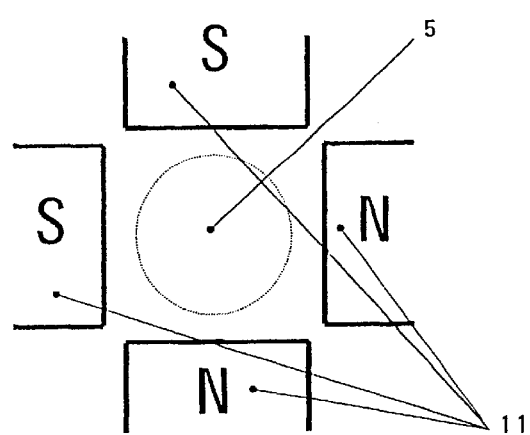
FIG. 8 shows a schematic view of an embodiment with magnetic deflection.
Figure 9:
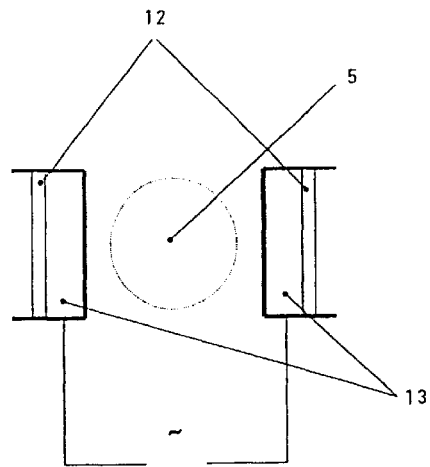
FIG. 9 shows a schematic view of an embodiment with electrical and magnetic deflection.

Advantageously as represented in FIGS. 7 to 9, similar to an oscilloscope, two pairs of cooperating electrodes 10 are provided which, for the achievement of their optimal action on the particles 1, are arranged between the outlet opening 9 and the vibration sensor 2, to the side of the path of the particle jet. By a corresponding drive of the two electrode pairs, preferably alike over the electronic switching arrangement 4, variable electric fields can be generated, by which the particle jet can be deflected in an arbitrary direction and about arbitrary angles, and in this manner can be led over the active collecting surface 5 of the vibration sensor 2. Preferably, closed paths are generated by this arrangement, for example circular paths or paths which arise from the superposing of two circular movements.

Figure 10:
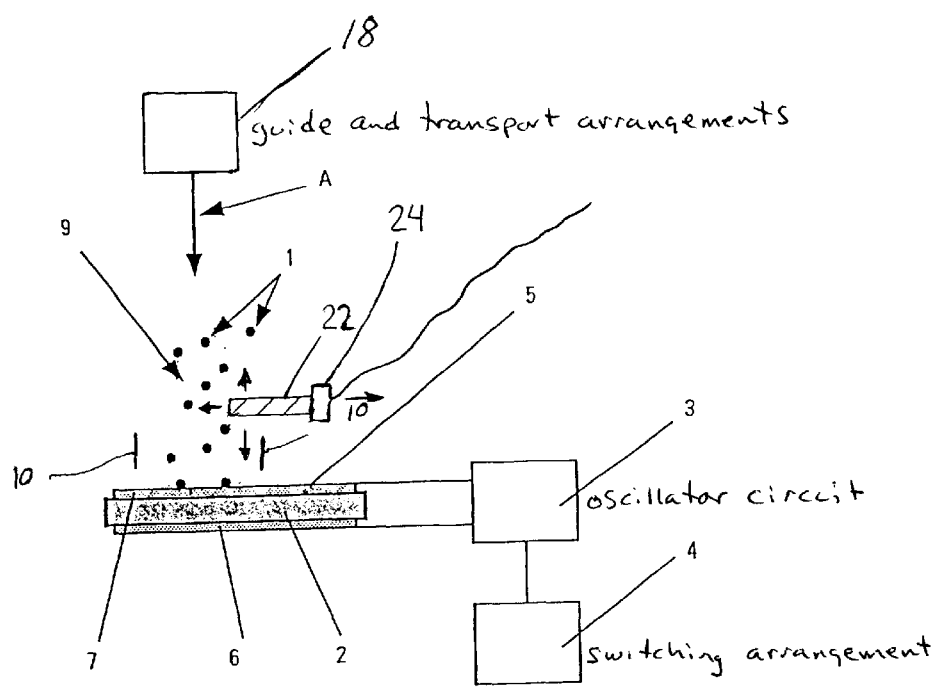
FIG. 10 shows a schematic representation of an embodiment with a corona needle.
Figure 11:
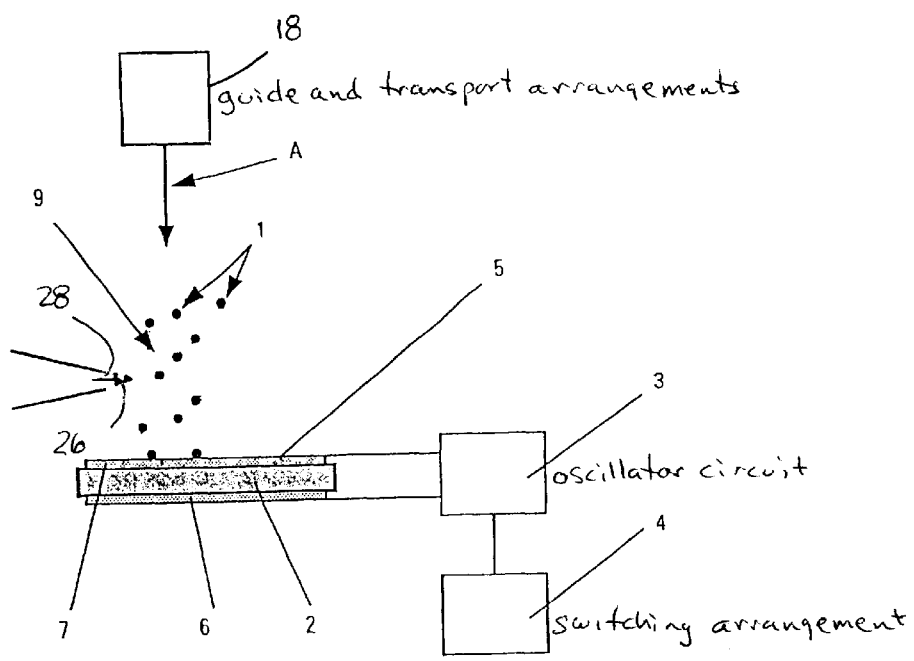
FIG. 11 shows a schematic representation of an embodiment with a neutral gas jet.

In the case of the electrostatic precipitation of the particles 1 on the active collecting surface 5 of the vibration sensor 2, there must be provided for its ionization a corona needle 22 (FIG. 10). By a movement of this corona needle or other structure over corresponding arrangements, if necessary over a movable bearing 24 of the corona needle, field characteristic of the needle can be changed, which again leads to an influence of the alignment and form of the particle jet passing the corona needle and emerging from the outlet opening. Here a movement of the corona needle is conceivable which is not only essentially parallel to the active collecting surface 5, but also essentially perpendicular to this collecting surface 5, or a movement that arises from a superposing of the earlier mentioned movements. This variant can be used alone or in combination with the earlier-described variation of an electrical, magnetic, or electromagnetic field for the deflection of the particle jet.

In FIG. 8 there is schematically represented a form of execution in which the deflection of the particle jet is achieved over the collecting surface 5 by means of an arrangement of two crossed pairs of magnets 11. An embodiment with a combination of electrical and magnetic deflection is represented in FIG. 9 and it can be especially advantageously used where smaller space requirement for the arrangement is necessary. Here, namely, only two arrangements lying opposite one another are necessary for the deflection of the particles over the collecting surface, which are constructed in each case from an electrode plate 13 with a magnetic winding 12 mounted on it or directly behind it. By use of different voltages on the electrode plates 13, there can be brought about a deflection in its connection direction, while the magnetic winding 12 generates a magnetic field likewise in a connection direction, which, however, brings about the desired deflection of the particles perpendicular thereto.

Finally, let there also be mentioned a further embodiment of the invention, in which the deflection of the particle jet is achieved by the means that a jet 26 (FIG. 11) of a neutral pure gas is led laterally onto the particle jet, and deflects the particle jet therefore with respect to the uninfluenced beam direction. Obviously, the amount of the pure gas must be taken into consideration in the determination of concentration, which can be ensured, for example, by means of flow sensors and their interrogation by the evaluating circuit arrangement 4. There, the pure gas is injected into the measuring chamber, preferably over at least one further outlet opening 28, the axis of which encloses an angle not equal to zero with the axis of the outlet opening 9 for the particle jet. If necessary, the outlet opening for the pure gas is adjustable in its direction and/or the flow speed of this pure gas is variable, in order to make possible a different influence of the particle jet. Alternatively or in addition to this, it would be possible by cooperation of two or more pure gas outlet openings, if necessary within each case alternating flow velocity, to achieve a deflection of the particle jet in more complex patterns, which allow a guidance of the particle jet over the active collecting surface 5 of the vibration sensor 2 also, for example, in closed paths, preferably circular paths or paths arising by superposition of several circular movements.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. An arrangement for the quantitative and qualitative analysis of particles in a gas, comprising: a measuring chamber with at least one entry opening for the gas to be analyzed, a vibrating system having at least one vibration sensor held essentially stationary relative to the measuring chamber, at least one collecting surface for the particles to be analyzed associated with the vibration sensor, an electrical circuit for the determination of characteristic vibration parameters of the vibrating system, guide and transport arrangements for the gas to be analyzed, and at least one active guiding or steering device for the particles contained in the gas.

2. An arrangement according to claim 1, wherein the particles are particles in the exhaust gas of an internal combustion engine.

3. An arrangement according to claim 1, wherein the collecting surface is provided on a piezoelectric resonator, which is integrated into the vibrating system and used as a vibration sensor.

4. An arrangement according to claim 1, wherein the active device comprises an orifice, the traversable cross sectional area of which is small as compared to the collecting surface, in combination with a device for moving the orifice relative to and essentially parallel to the collecting surface.

5. An arrangement according to claim 4, wherein the device for moving the orifice moves the orifice in a closed path.

6. An arrangement according to claim 4, wherein the device for moving the orifice moves the orifice in an essentially circular path, in which an axis of the circular path is oriented essentially perpendicular to the collecting surface of the vibration sensor.

7. An arrangement according to claim 6, wherein at least one of the vibration sensor and its collecting surface is constructed rotationally symmetrical about the axis of the circular path.

8. An arrangement according to claim 4, wherein the device for moving the orifice moves the orifice relative to the vibration sensor with alternating speed.

9. An arrangement according to claim 4, wherein the device for moving the orifice moves the orifice relative to the vibration sensor with alternating angular velocity.

10. An arrangement according to claim 4, wherein a first gas jet flows through the orifice comprising a first outlet opening during operation along an axis and the active device comprises at least one additional outlet opening for an additional jet to flow through along a second axis, the axes of the two outlet openings preferably enclosing with one another an angle not equal to zero.

11. An arrangement according to claim 10, wherein the additional outlet opening is located near the collecting surface of the vibration sensor.

12. An arrangement according to claim 1, wherein the active device comprises a corona needle which is coupled together with a device for its movement relative to the vibration sensor.

13. An arrangement according to claim 1, wherein the active device comprises at least one device for the generation of at least one of a variable electric, magnetic or electromagnetic field between the entry opening and the collecting surface, and a device for imparting an electrical charge on the particles in the gas.

14. An arrangement according to claim 1, wherein the active device is designed for the generation of at least one of an alternating flow speed or direction of a jet of the gas to be analyzed.

15. An arrangement according to claim 14, wherein the active device is designed for the generation of at least one of alternating gas or particle velocities in the entry opening.

16. A process for the quantitative and qualitative analysis of particles in a gas, comprising the steps of precipitating particles in a jet through at least one outlet opening onto at least one collecting surface of at least one essentially stationary vibration sensor of a vibrating system, determining a change in characteristic vibration parameters of said vibration sensor on a basis of the particle precipitation, and actively moving the particle jet over an ever alternating zone of the collecting surface of the vibration sensor.

17. A process according to claim 16, wherein said gas comprises an exhaust gas of an internal combustion engine.

18. A process according to claim 16, wherein said vibration sensor comprises a piezoelectric resonator.

19. A process according to claim 16, including the step of guiding the particle jet along a closed curve.

20. A process according to claim 16, including the step of guiding the particle jet along a circular path.

21. A process according to claim 16, including the step of guiding the particle jet along a curve which arises by superposition of at least two rotary movements with axes of rotation essentially perpendicular to the active collecting surface.

22. A process according to claim 16, including the step of guiding the particle jet with alternating speed.

23. A process according to claim 16, including the step of guiding the particle jet with alternating angular velocity.

24. A process according to claim 16, including the steps of utilizing an electric field to ionize the particles and deflecting and guiding the particle jet by at least one of alternating electrical, magnetic, or electromagnetic fields.

25. A process according to claim 24, including the step of continuously varying the electric field used for the ionization of the particles in the gas.

26. A process according to claim 16, including the step of deflecting the particle jet by directing a gas jet of at least one of alternating flow speed and direction onto the particle jet.

27. A process according to claim 16, including the step of aiming the gas jet containing the particles with at least one of an alternating flow speed and flow direction onto the collecting surface of the vibration sensor.

28. A process according to claim 16, including the step of directing the particles through the outlet opening with alternating speed.

* * * * *